United States Patent [19]
Hart et al.

[11] Patent Number: 5,276,046
[45] Date of Patent: Jan. 4, 1994

[54] HYDRAZINE DERIVATIVES

[75] Inventors: Terance W. Hart; Brian W. Sharp; Roger J. A. Walsh, all of Dagenham, United Kingdom

[73] Assignee: Rhone-Poulenc Rorer Limited, Eastbourne, England

[21] Appl. No.: 916,869

[22] PCT Filed: Feb. 8, 1991

[86] PCT No.: PCT/EP91/00248
§ 371 Date: Aug. 7, 1992
§ 102(e) Date: Aug. 7, 1992

[87] PCT Pub. No.: WO91/12241
PCT Pub. Date: Aug. 22, 1991

[30] Foreign Application Priority Data

Feb. 8, 1990 [GB] United Kingdom ............... 9002848

[51] Int. Cl.$^5$ ............................................ C07D 213/53
[52] U.S. Cl. .................................... 514/357; 546/332; 564/271; 514/641
[58] Field of Search ................ 546/332; 514/357, 641; 564/271

[56] References Cited

FOREIGN PATENT DOCUMENTS 0321274  6/1989  European Pat. Off. .

*Primary Examiner*—C. Warren Ivy
*Assistant Examiner*—Zinna N. Davis
*Attorney, Agent, or Firm*—James A. Nicholson; Martin F. Savitzky; Raymond S. Parker, III

[57] ABSTRACT

A hydrazine derivative of formula (I),

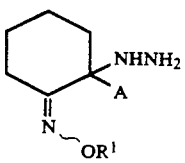

(I)

wherein A represents an optionally substituted phenyl, naphthyl or heteroaromatic group containing one or two nitrogen atoms, and $R^1$ represents hydrogen, optionally substituted alkyl, or optionally substituted benzyl, phenethyl, or 1-naphthylmethyl, or pyrid-3-ylmethyl group, and salts thereof, possess useful pharmaceutical properties.

7 Claims, No Drawings

HYDRAZINE DERIVATIVES

This invention relates to new therapeutically useful hydrazine derivatives, to processes for their preparation and to pharmaceutical compositions containing them.

The new hydrazine derivatives of the present invention are those compounds of formula (I), hereinafter depicted wherein:

A represents:

(1) a phenyl or naphthyl group which is optionally substituted by one or more substituents selected from halogen atoms and alkyl, aryl, arylalkyl, cyano, nitro, trifluoromethyl, carbamoyl, carboxy, alkoxycarbonyl and alkylsulphonyl groups; or (2) a heteroaromatic group containing 1 or 2 nitrogen atoms, selected from pyrid-3-yl, quinolin-3-yl, isoquinolin-4-yl, pyridazin-4-yl, pyrimidin-5-yl, pyrazin-3-yl, indol-3-yl and thiazol-5-yl, optionally substituted by one or more substituents selected from alkyl and alkoxy groups and halogen atoms; and $R^1$ represents either:

i) a hydrogen atom;

ii) an alkyl group which is unsubstituted or substituted by one or more substituents selected from $C_{2-4}$-alkenyl, carboxy, alkoxycarbonyl, hydroxy, alkoxy, amino, alkylamino and dialkylamino groups, and from carbamoyl groups which may be unsubstituted or substituted by one or two alkyl groups; or iii) a benzyl, phenethyl, 1-naphthylmethyl, 2-naphthylmethyl or pyrid-3-ylmethyl group, each of which may be substituted on the ring by one or more substituents selected from halogen atoms and hydroxy, alkyl, cyano, nitro, trifluoromethyl, carboxy, alkylamino, alkanoylamino and alkoxycarbonyl groups and from alkoxy groups (which themselves are unsubstituted or substituted by one or more substituents selected from $C_{2-4}$-alkenyl, carboxy, alkoxycarbonyl, hydroxy, alkoxy, amino, alkylamino and dialkylamino groups, and from carbamoyl groups which may be unsubstituted or substituted by one or two alkyl groups); and pharmaceutically acceptable salts thereof.

In this specification all alkyl groups and alkyl moieties can be straight-chain or branched, and, unless otherwise specified, contain one to about four carbon atoms; and all aryl groups and aryl moieties, unless otherwise specified, are preferably phenyl or naphthyl groups which may be substituted by one or more substituents selected from alkyl and alkoxy groups and halogen atoms.

A preferably represents a heteroaromatic group as hereinbefore defined, preferably a pyrid-3-yl group, $R^1$ preferably represents a benzyl group and the oxyimino group is preferably in the anti-configuration.

In certain cases the substituents A and $R^1$ can contribute to stereoisomerism. All such forms are embraced by the present invention.

A particularly important compound of the present invention is:

A anti-2-benzyloxyimino-1-hydrazino-1-(pyrid-3-yl)cyclohexane dihydrochloride

The letter A is allocated for ease of reference in other parts of the specification.

The compounds have valuable pharmacological properties, in particular properties which are indicative of utility in the treatment and/or prophylaxis of disorders associated with:

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastrointestinal tract, urinary bladder and uterus, including peptic ulcers, irritable bowel syndrome and diverticular disease; and premature labour.

The compounds also have utility in the inhibition of head hair loss associated with male pattern baldness, by topical application.

Compounds within the scope of the present invention exhibit positive pharmacological activities as demonstrated by tests which are believed to correlate to pharmacological activity in humans and other animals.

For example, compounds of general formula (I) were submitted to:

Vaso-relaxant Activity Test

The test method used was adapted from those described by Winslow et al [Eur. J. Pharmacol., 131, 219–228 (1986)] and Karaki [J. Pharmacol. Methods, 18, 1–21 (1987)] for differentiating vaso-relaxant activity.

Thoracic aorta was removed from rats and transverse strips, denuded of endothelium, were suspended in a bath containing Krebs solution. The tension was recorded and a contraction induced by addition of 20 mM $K^+$ (potassium ion) to the bathing solution. The test compound was added to the bath as a solution in increasing cumulative concentration. The concentration in the bathing solution of the compound A which reduced the $K^+$-induced contraction by 90% was determined and, expressed as the effective concentration ($EC_{90}$), had a value of 2 $\mu M$.

The compounds of general formula (I) can be prepared by the application and adaptation of known methods, for example as hereinafter identified. By the term "known methods" as used in this specification is meant methods heretofore used or described in the literature.

According to a feature of the present invention, compounds of general formula (I), wherein A and $R^1$ are as hereinbefore defined, are prepared by the hydrolysis and decarboxylation of a compound of formula (II), wherein A and $R^1$ are as hereinbefore defined and each $R^2$ represents alkyl, as hereinbefore defined, and is preferably t-butyl. The reaction is typically carried out in an inert solvent, such as an ether (e.g. diethyl ether or dioxan) or mixtures thereof, at temperatures from room temperature to the reflux temperature, using an acidic reagent, such as hydrogen chloride.

The starting materials and intermediates can be made by the application or adaptation of known methods or are readily available.

For example, compounds of formula (II), wherein A, $R^1$ and $R^2$ are as hereinbefore defined, can be prepared by the reaction of a compound of formula (III), wherein A and $R^2$ are as hereinbefore defined, with a compound of general formula:

$$NH_2-O-R^1 \qquad (IV)$$

wherein $R^1$ is as hereinbefore defined, or with an acid addition salt (preferably the hydrochloride) thereof.

The reaction is generally carried out in the presence of an inorganic base, e.g. sodium carbonate or sodium acetate in an inert organic solvent, e.g. ethanol, or an organic base, e.g. pyridine, which may serve as the solvent, in an otherwise inert organic solvent at a temperature from 0° C. to 120° C.

Compounds of formula (III), wherein A and $R^2$ are as hereinbefore defined, can be prepared by the reaction of a compound of formula (VI), wherein A is as hereinbefore defined, with a compound of formula:

$$R^2O_2CN=NCO_2R^2 \qquad (V)$$

wherein $R^2$ is as hereinbefore defined.

The reaction is generally carried out in the presence of a base, such as potassium t-butoxide, in an inert solvent, such as dimethylformamide, at or below room temperature.

Compounds of formula (VI), wherein A is as hereinbefore defined, can be made via a dehydrobromination/rearrangement reaction of compounds of formula (VII), wherein A is as hereinbefore defined. This may be initiated by a bromide extracting agent such as a silver salt (e.g. silver perchlorate) and carried out in an inert anhydrous solvent (for example an ether such as tetrahydrofuran).

Compounds of formula (VII), wherein A is as hereinbefore defined, can be made by the addition of hypobromous acid across the double bond of compounds of formula (VIII), wherein A is as hereinbefore defined. This may be carried out by reaction with a brominating agent (e.g. 1,3-dibromo-5,5-dimethylhydantoin) in an aqueous acidic medium, optionally in the presence of a cosolvent.

Compounds of formula (VIII), wherein A is as hereinbefore defined, can be made via a coupling reaction between a phosphorane of formula (IX) (typically made in situ by the reaction of a compound of formula (X), wherein $R^3$ and Z are conventional groups present in a Wittig reagent and its phosphonium salt precursor [e.g. phenyl and bromine respectively], with a strong base, such as potassium t-butoxide, in an anhydrous solvent, such as tetrahydrofuran, preferably under an inert atmosphere) and a compound of formula:

$$A-CHO \qquad (XI)$$

wherein A is as hereinbefore defined.

Alternatively compounds of formula (VI), wherein A is as hereinbefore defined, can be made by the removal of methanol from compounds of formula (XII), wherein A is as hereinbefore defined. This is typically carried out in the presence of a strongly acidic agent (e.g. phosphorus pentoxide or sulphuric acid), optionally in a solvent (such as toluene) and at elevated temperature, followed by hydrolysis of the intermediate enol ether.

Compounds of formula (XII) can be made by reaction of a compound of formula:

$$A\text{-Hal} \qquad (XIII)$$

wherein A is as hereinbefore defined and Hal represents a halogen, preferably bromine or chlorine, atom, in the presence of a strong base, such as an alkyl lithium (e.g. butyllithium), with 2-methoxycyclohexanone in an inert solvent such as an ether (e.g. diethyl ether) or a hydrocarbon (e.g. toluene).

It will be understood that it may be desirable to change one or more of the substituents on the alkyl or aryl groups at an appropriate stage during the synthesis of the compounds of the invention. For example, the compounds of general formula (I) wherein A represents a phenyl group substituted by a carbamoyl group are alternatively prepared from the corresponding compounds of general formula (I) wherein A represents a phenyl group substituted by a cyano group by the application or adaptation of known methods for such conversion.

It is to be understood that the conversion, for example by known methods, of one compound of general formula (I) into another compound of formula (I) constitutes a feature of the present invention.

By the term "pharmaceutically acceptable salts" as used in this specification is meant salts the anions or cations of which are relatively innocuous to the animal organism when used in therapeutic doses so that the beneficial pharmaceutical properties of the parent compounds of general formula (I) capable of forming salts are not vitiated by side-effects ascribable to those anions or cations.

It is to be understood that, where in this specification reference is made to compounds of formula (I), it is intended to refer also, where the context so permits, to their pharmaceutically acceptable salts.

Suitable acid addition salts for use in pharmaceuticals may be selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-β-hydroxynaphthoates, gentisates and di-p-toluoyltartrates.

Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts.

As well as being useful in themselves as active compounds, salts of the compounds of general formula (I) are useful for the purposes of purification of the parent compounds of general formula (I), for example by exploitation of the solubility differences between the salts and the parent compounds, by techniques well known to those skilled in the art.

The compounds obtained by the above processes can be purified by the usual physical methods, in particular crystallization and chromatography.

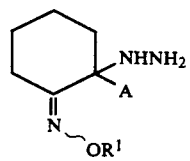

(I)

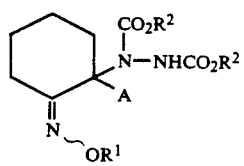

(II)

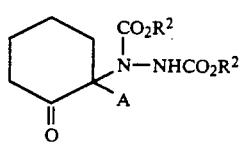

(III)

-continued

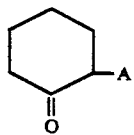 (VI)

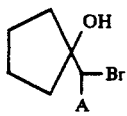 (VII)

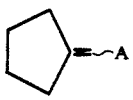 (VIII)

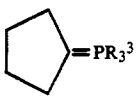 (IX)

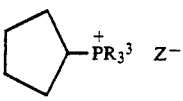 (X)

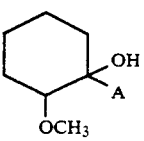 (XII)

The following Example illustrates the preparation of compounds according to the present invention.

All N.M.R spectra were recorded at 200 MHz. The chemical shifts are expressed in ppm relative to tetramethylsilane. Abbreviations in the text are as follows: s=singlet, d=doublet, dd=doublet of doublets, ddd=doublet of doublets of doublets, m=multiplet, c=unresolved complex peak, br=broad signal.

EXAMPLE 1

Compound A

A solution of anti-2benzyloxyimino-1-(N,N'-di-t-butoxycarbonylhydrazino)-1-(pyrid-3-yl)cyclohexane (3.8 g, 7.4 mmol) in dioxan (100 ml) was treated with a solution of hydrogen chloride (4.55 g, 125 mmol) in ether (25 ml). The mixture was then heated at 90° C. for 3 minutes. After cooling, the precipitated product was filtered off, washed with ether (3×20 ml) and then dried (20° C.; 14 mmHg) to give anti-2-benzyloxyimino-1-hydrazino-1-(pyrid-3-yl)cyclohexane dihydrochloride (2.2 g, 5.6 mmol), m.p. 193°-194° C.;

Found: C, 54.7; H, 6.2; Cl, 18.7; N, 14.1% Calculated for $C_{18}H_{22}N_4O.2HCl.H_2O$: C, 55.1; H, 6.4; Cl, 18.1; N, 14.3%.

REFERENCE EXAMPLE 1

A solution of 2-(N,N'-di-t-butoxycarbonylhydrazino)-2-(pyrid-3-yl)cyclohexane (4.05 g, 10 mmol) and O-benzylhydroxylamine hydrochloride (3.2 g, 20 mmol) in pyridine (25 ml) was stirred at 60° C. for 48 hrs. The mixture was then concentrated in vacuo, heated with toluene (30 ml) and reconcentrated to give a crude oil which was partitioned between chloroform (25 ml) and saturated aqueous sodium bicarbonate solution. The organic phase was washed with brine (20 ml) and dried over magnesium sulphate. After concentration the crude oil was crystallised from petroleum ether (60°-80° C.) to give anti-2-benzyloxyimino-1-(N,N'-di-t-butoxycarbonylhydrazino)-1-(pyrid-3-yl)cyclohexane (3.0 g, 5.9 mmol), m.p. 96°-97° C.;

Found: C, 64.9; H, 7.5; N, 10.6; $H_2O$, 2.1% Calculated for $C_{28}H_{38}N_4O_5.\frac{1}{2}H_2O$: C, 64.7; H, 7.6; N, 10.8; $H_2O$, 1.7%.

REFERENCE EXAMPLE 2

Potassium t-butoxide (3.7 g, 33 mmol) was added, in one portion, to a stirred solution of 2-(pyrid-3-yl)cyclohexanone (5.3 g, 30 mmol) in dimethylformamide (60 ml) at 0° C. After 60 minutes the dark red solution was treated with di-t-butyl diazodicarboxylate (7.6 g, 33 mmol) over 5 minutes. The mixture was then allowed to warm to 20° C. over 1 hour, poured into saturated ammonium chloride solution (50 ml) and extracted with ethyl acetate (2×25 ml). The combined organic extracts were successively washed with water (20 ml) and saturated brine (20 ml) and dried over sodium sulphate. Concentration in vacuo gave the crude product which was recrystallised from petroleum ether (60°-80° C.; 150 ml) to give 2-(N,N'-di-t-butoxycarbonylhydrazino)-2-(pyrid-3-yl)cyclohexanone (7.1 g, 17.5 mmol), m.p. 123°-125° C.;

Found: C, 62.0; H, 8.0; N, 10.0% Calculated for $C_{21}H_{31}N_3O_5$: C, 62.2; H, 7.7; N, 10.4%.

REFERENCE EXAMPLE 3

A solution of (±)-trans-1-[(pyrid-3-yl)-bromomethyl]cyclopentanol (10.24 g, 40 mmol) in anhydrous tetrahydrofuran (500 ml) at 0° C. was treated, dropwise during 30 minutes, with a solution of silver perchlorate (9.9 g, 48 mmol) in anhydrous tetrahydrofuran (50 ml). After 60 minutes at 0° C. the mixture was poured into a mixture of saturated aqueous brine solution (500 ml) and 10% w/v aqueous sodium bicarbonate solution (500 ml). The resulting mixture was filtered and then extracted with ethyl acetate (2×500 ml). The combined organic extracts were washed with brine and then dried over sodium sulphate. Concentration in vacuo (30° C.; 14 mmHg) gave a crude oil which was recrystallised from cyclohexane (120 ml) to give (±)-2-(pyrid-3-yl)-cyclohexanone (6.7 g, 38 mmol), m.p. 78°-80° C.;

N.M.R. ($CDCl_3$): 1.72–2.12 (m, 4H), 2.12–2.40 (m, 2H), 2.40–2.64 (m, 2H), 3.56–3.72 (dd, 1H), 7.22–7.32 (m, 1H), 7.44–7.54 (ddd, 1H), 8.34–8.42 (dd, 1H), 8.46–8.54 (dd, 1H).

REFERENCE EXAMPLE 4

A solution of 3-cyclopentylidenemethylpyridine (62.2 g, 0.39 mol) in acetone (600 ml) and water (100 ml) was treated with a solution of concentrated sulphuric acid (18.9 g, 0.19 mol) in water (100 ml) at 5° C. The ice-cold solution was treated with 1,3-dibromo-5,5-dimethylhydantoin (55 g, 0.19 mol) during 20 minutes. After 3.5 hours at 0° C. the mixture was treated with sodium bicarbonate (33.6 g, 0.4 mol) followed by water (2 1) and then extracted with ethyl acetate (2×500 ml). The organic phase was removed and washed with 10% w/v aqueous sodium bicarbonate solution (500 ml) followed by water (200 ml) and brine (200 ml). The crude extract was dried over sodium sulphate and then filtered through a column of flash silica gel (10 cm×2.4 cm diameter). After concentration in vacuo (20° C.; 14 mmHg) the dark oil crystallised on standing to give (±)-trans-1-[(pyrid-3-yl)bromomethyl]cyclopentanol (56 g, 0.22 mol) m.p. 92°–94° C.;

N.M.R. (CDCl$_3$): 1.36–2.06 (c, 8H), 2.32–2.46 (br s, 1H), 5.02 (s, 1H), 7.24–7.34 (ddd, 1H), 8.0–8.1 (ddd, 1H), 8.52–8.56 (dd, 1H), 8.62–8.66 (d, 1H)

Found: C, 51.9; H, 5.6; Br, 30.6; N, 5.5% Calculated for C$_{11}$H$_{14}$BrNO: C, 51.6; H, 5.5; Br, 31.2; N, 5.5%.

REFERENCE EXAMPLE 5

A suspension of cyclopentyltriphenylphosphonium bromide (226 g, 0.55 mol) in anhydrous tetrahydrofuran (1000 ml) at 2° C. was treated with vigorous stirring under an atmosphere of argon, with potassium t-butoxide (61.7 g, 0.55 mol). The dark red mixture was stirred at 5° C. for 80 minutes and then treated with pyridine-3-carbaldehyde (58.9 g, 0.55 mol) during a period of 20 minutes. The reaction mixture was stirred at 0° C. for 2 hours and then at 20° C. for 18 hours. The tetrahydrofuran was removed in vacuo (30° C.; 14 mmHg) and the residue extracted with pentane (2×500 ml). After treatment with decolourising charcoal (5 g), the mixture was filtered through silica gel. The filtrate was concentrated in vacuo (30° C., 14 mmHg; then 20° C., 0.01 mmHg) to give 3-cyclopentylidenemethylpyridine (54 g, 0.34 mol) as an orange oil which was used without further purification;

N.M.R. (CDCl$_3$): 1.6–1.95 (m, 4H), 2.4–2.65 (m, 4H), 6.26–6.34 (m, 1H), 7.16–7.25 (ddd, 1H), 7.56–7.65 (ddd, 1H), 8.52–8.52 (d, 1H).

REFERENCE EXAMPLE 6A

A 4:1 mixture of (±)-cis/trans-2-methoxy-1-(pyrid-3-yl)cyclohexanol (2 g, 10 mmol), toluene and phosphorus pentoxide (3.4 g, 24 mmol) was heated at reflux for 5 hours. The mixture was then filtered and the precipitate partitioned between 2M sodium hydroxide solution (80 ml) and diethyl ether (25 ml). The aqueous layer was extracted with ether (3×25 ml) and the combined organic extracts were dried over sodium sulphate. Concentration in vacuo gave a crude oil which was purified by flash chromatography to give 2-(pyrid-3-yl)cyclohexanone (0.7 g, 4 mmol).

REFERENCE EXAMPLE 6B (+)-cis/trans-2-Methoxy-1-(pyrid-3-yl)cyclohexanol (270.6 g) was added dropwise to concentrated sulphuric acid (1.6 l). The temperature rose to 40° C. and cold water cooling was used to prevent this being exceeded. The dark red/brown solution was stirred for 6.5 hours as its temperature fell to 28° C.

The solution was added to vigorously stirred ice/water (15 l) and the brown mixture stirred for 10 minutes until its temperature had dropped to −5° C. Aqueous sodium hydroxide (12M, 4.82 l) was added over 30 minutes until the pH reached 5. A further 10 l of ice was added during this addition to prevent the temperature rising above 30° C. Sodium carbonate (88 g) was then added portionwise to pH8, followed by sodium chloride (5.3 kg).

Diethyl ether (5 l) was added and the mixture stirred vigorously. The ether was separated and the aqueous layer extracted with further quantities of diethyl ether (5 l + 4 l + 3 l + 2 l). The combined extracts were dried (MgSO$_4$) and evaporated to give a yellow solid. This was triturated with diethyl ether (500 ml) to give 2-(pyrid-3-yl)cyclohexanone (200 g) as a cream solid.

REFERENCE EXAMPLE 7

To a solution of 2.5M n-butyllithium in hexane (13.2 ml, 33 mmol) at −78° C. was added diethyl ether (15 ml) followed by a solution of 3-bromopyridine (4.7 g, 30 mmol) in ether (90 ml) over a period of 10 minutes. After 1 hour at −78° C. a solution of (+)-2-methoxycyclohexanone (3.84 g, 30 mmol) in ether (20 ml) was added dropwise during 10 minutes. After 2 hours at −78° C. and 30 minutes at 0° C. the reaction mixture was warmed to 20° C. and then poured onto ice (150 g). The mixture was extracted with ether (2×50 ml) and then the combined organic extracts were extracted with hydrochloric acid (1M, 50 ml). This aqueous extract was washed with ether (20 ml) and then treated with sodium hydroxide solution (2M, 25 ml) and extracted with ether (3×100 ml). The organic extracts were combined, washed with brine then dried over anhydrous sodium sulphate. Concentration in vacuo gave (+)-2-methoxy-1-(pyrid-3-yl)cyclohexanol (5.0 g, 24 mmol) as a 4:1 mixture of cis and trans isomers;

N.M.R. (CDCl$_3$): 1.2–2.14 (c), 2.24–2.44 (m), 2.90–3.28 (c), 3.48–3.60 (m), 7.18–7.30 (m), 7.78–7.96 (m), 8.40–8.48 (m), 8.62–8.72 (m), 8.78–8.82 (m).

The present invention includes within its scope pharmaceutical compositions which comprise a compound of general formula (I) or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose.

The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting, and suspending agents, and sweetening, flavouring, perfuming and preserving agents. The compositions according to the invention for oral administration also include capsules of absorbable material such as gelatin, containing one or more of the active substances with or without the addition of diluents or excipients.

Compositions according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilising, preserving, wetting, emulsifying and dispersing agents. They may be sterilised by, for example, filtration through a bacteria-retaining filter, by incorporation in the compositions of sterilising agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulised or dry powders formulated in accordance with known methods.

Solid compositions for rectal administration include suppositories formulated in accordance with known methods and containing one or more of the compounds of formula (I) or a pharmaceutically acceptable salt thereof.

The percentage of active ingredient in the composition of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration, the duration of the treatment and the condition of the patient. In the adult, the doses are generally from about 0.001 to about 50, preferably from about 0.01 to about 5, mg/kg body weight per day by oral administration. By inhalation, either as a nebulised solution or as a formulated dry powder, the preferred daily dosage is from about 0.001 to about 5, preferably from about 0.01 to about 0.5, mg/kg body weight.

The compounds may also be applied topically for inhibition of head hair loss associated with male pattern baldness, the preferred daily dosage being from about 0.1 to about 10 mg/kg body weight applied, for example, in 5 ml portions two or three times per day.

The following Example illustrates pharmaceutical compositions according to the present invention.

COMPOSITION EXAMPLE

No. 2 size gelatin capsules each containing:

| | |
|---|---|
| anti-2-benzyloxyimino-1-hydrazino-1-(pyrid-3-yl)-cyclohexane dihydrochloride | 20 mg |
| lactose | 100 mg |
| starch | 60 mg |
| dextrin | 40 mg |
| magnesium stearate | 1 mg | were prepared in accordance with the usual procedure.

We claim:

1. A hydrazine compound of the formula:

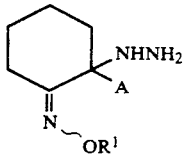

wherein

A is:

(1) phenyl or naphthyl which are unsubstituted or substituted by one or more of halogen, alkyl, cyano, nitro, trifluoromethyl, carbamoyl, carboxy, alkoxycarbonyl, alkylsulphonyl, phenyl, naphthyl, phenylalkyl, naphthylalkyl, phenyl substituted by one or more of straight- or branched- chain $C_{1-4}$-alkyl, $C_{1-4}$-alkoxy and halogen or naphthyl substituted by one or more of straight- or branched-chain $C_{1-4}$-alkyl, $C_{1-4}$-alkoxy and halogen; or (2) pyrid-3-yl, quinolin-3-yl, isoquinolin-4-yl, pyridazin-4-yl, pyrimidin-5-yl, pyrazin-3-yl, indol-3-yl or thiazol-5-yl, each of which are unsubstituted or substituted by one or more of straight- or branched-chain $C_{1-4}$-alkyl, $C_{1-4}$-alkoxy and halogen; and $R_1$ is:

(i) hydrogen;

(ii) straight- or branched-chain $C_{1-4}$-alkyl which is unsubstituted or substituted by one or more of $C_{2-4}$-alkenyl, carboxy, alkoxycarbonyl, hydroxy, alkoxy, amino, alkylamino, dialkylamino, carbamoyl, alkylcarbamoyl and dialkylcarbamoyl; or (iii) benzyl, phenethyl, 1-naphthylmethyl, 2-naphthylmethyl or pyrid-3-ylmethyl each of which are unsubstituted or substituted on the ring by one or more of halogen, hydroxy, alkyl, cyano, nitro, trifluoromethyl, carboxy, alkylamino, alkanoylamino, alkoxycarbonyl, alkoxy, carbamoyl, alkoxy substituted by one or more of $C_{2-4}$-alkenyl, carboxy, alkoxycarbonyl, hydroxy, alkoxy, amino, alkylamino or dialkylamino and carbamoyl substituted by one or two straight- or branched-chain $C_{1-4}$-alkyl groups; or a pharmaceutically acceptable salt thereof.

2. A compound according to claim 1, wherein A represents a pyrid-3-yl group.

3. A compound according to claim 1, wherein $R^1$ represents a benzyl group.

4. A compound according to claim 1, wherein the oxyimino group is in the anti-configuration.

5. A compound according to claim 4 which is anti-2-benzyloxyimino-1-hydrazino-1-(pyrid-3-yl)cyclohexane or a pharmaceutically acceptable salt thereof.

6. A pharmaceutical composition for the treatment and/or prophylaxis of disorders associated with vascular smooth muscle contraction; respiratory smooth muscle contraction; contraction of smooth muscle of gastrointestinal tract, urinary bladder and uterus; which comprises an effective amount to ameliorate said disorder of a compound of claim 1 or a pharmaceutically acceptable salt thereof in association with a pharmaceutical carrier or coating.

7. A pharmaceutical composition for the inhibition and/or prophylaxis of head hair loss associated with male pattern baldness which comprises an effective amount to inhibit said loss of a compound of claim 1 or a pharmaceutically acceptable salt thereof in association with a pharmaceutical carrier or coating.

* * * * *